US012810969B2

(12) United States Patent
Han et al.

(10) Patent No.: US 12,810,969 B2
(45) Date of Patent: Nov. 24, 2026

(54) METHOD FOR PREDICTING POTENTIAL ENERGY OF MULTICOMPONENT MATERIALS

(71) Applicants: Hyundai Motor Company, Seoul (KR); Kia Corporation, Seoul (KR); UIF (University Industry Foundation), Yonsei University, Seoul (KR)

(72) Inventors: Byungchan Han, Seoul (KR); Seunghyo Noh, Uiwang-si (KR); Minjoon Hong, Seoul (KR); Hoje Chun, Seoul (KR)

(73) Assignees: HYUNDAI MOTOR COMPANY, Seoul (KR); KIA CORPORATION, Seoul (KR); UIF (University Industry Foundation), Yonsei University, Seoul (KR)

( * ) Notice: Subject to any disclaimer, the term of this patent is extended or adjusted under 35 U.S.C. 154(b) by 356 days.

(21) Appl. No.: 18/522,562

(22) Filed: Nov. 29, 2023

(65) Prior Publication Data

US 2024/0404647 A1 Dec. 5, 2024

(30) Foreign Application Priority Data

May 25, 2023 (KR) ........................ 10-2023-0067511

(51) Int. Cl.
*G16C 20/30* (2019.01)
*G16C 20/70* (2019.01)

(52) U.S. Cl.
CPC ............. *G16C 20/30* (2019.02); *G16C 20/70* (2019.02)

(58) Field of Classification Search
CPC ......... G16C 60/00; G16C 20/70; G16C 20/30
See application file for complete search history.

(56) References Cited

U.S. PATENT DOCUMENTS

| | | | | |
|---|---|---|---|---|
| 10,923,214 | B2 * | 2/2021 | Fan | G16C 20/70 |
| 11,514,349 | B1 * | 11/2022 | Rei | G06N 7/01 |
| 12,511,526 | B2 * | 12/2025 | Noh | G06N 3/065 |
| 2022/0165364 | A1 * | 5/2022 | Qiao | G06N 3/096 |
| 2022/0405563 | A1 | 12/2022 | Noh | |

FOREIGN PATENT DOCUMENTS

| | | |
|---|---|---|
| KR | 10-2022-0132873 A | 10/2022 |
| KR | 10-2022-0169128 A | 12/2022 |

* cited by examiner

*Primary Examiner* — An H Do
(74) *Attorney, Agent, or Firm* — MCDONNELL BOEHNEN HULBERT & BERGHOFF LLP

(57) ABSTRACT

The present disclosure provides a method for predicting a potential energy of a multicomponent material. The method includes encoding a structural information of a multicomponent material in which eigenvector values for each element are calculated using an atom-centered symmetry function (ACSF) of a structural information of atoms constituting the multicomponent material. The method also includes calculating a bond order potential (BOP) parameter for each element using the calculated eigenvector value as an input value and using a different artificial neural network model for each type of atom to construct a physics-informed artificial neural network (PINN) model. The method also includes calculating a bond order potential value for each element to construct a potential energy surface (PES). The method also includes performing structural optimization or physical property prediction of the multicomponent material using a potential energy surface.

9 Claims, 11 Drawing Sheets

METHOD FOR PREDICTING POTENTIAL ENERGY OF MULTICOMPONENT MATERIALS

CROSS-REFERENCE TO RELATED APPLICATIONS

This application claims priority to and the benefit of Korean Patent Application No. 10-2023-0067511 filed in the Korean Intellectual Property Office on May 25, 2023, the entire contents of which are incorporated herein by reference.

TECHNICAL FIELD

This description relates to a method for predicting a potential energy of a multicomponent material using an artificial neural network.

BACKGROUND

Accurate understanding of properties of various materials such as polymers, macromolecules, and compounds is crucial for all decisions throughout the entire process of production and consumption of the corresponding molecules such as reviewing usability, designing their synthesis and purification, and establishing methods and conditions of storage, transportation, use, disposal, etc. and thus industrially and academically very important issues.

The properties of molecules may be obtained most directly through an experiment but requires considerable costs and time in various aspects such as preparing purified samples and establishing an environment for accurate measurements but in some cases, not possible to obtain. Accordingly, various alternatives such as mathematical modeling and computational simulation, etc. have been proposed.

In order to construct a prediction model, there have been attempts to use an artificial neural network. An artificial neural network technology is intended to create a mechanical learning method that imitates an operation mechanism of human nerve cells and has been used for information processing in various fields since its emergence in the mid-$20^{th}$ century.

FIG. 1 shows a typical example of an artificial neural network. The artificial neural network consists of an input layer accepting input data, an output layer creating output data, and a hidden layer disposed therebetween, wherein each layer consists of one or more nodes. Each node of the hidden layer is interconnected with the nodes of the input layer and the output layer by weight values ($w_{ij}$, $w'_{ij}$). Each node of the hidden layer and the output layer receives input values from the nodes of the prior step, computes them into output values, wherein activation functions $f_1$ and $f_2$ are applied.

In order to apply this artificial neural network theory to an actual information processing technology, required is a process of training a computer by using a sample that combines various input values and the corresponding output values, that is, a training set. Specifically, a weight value for each connection point may be optimized by using a back-propagation algorithm to minimize a difference between computed values by the artificial neural network for given input values and actual values. The artificial neural network, which has once completed this training and then, may autonomously establish rules without being not separately provided with rules or knowledge needed to solve problems and quickly derive plausible output values for arbitrary input values, is used as a very useful tool for too difficult tasks to be realized by using the existing theories such as predicting physical properties with respect to large quantities of unknown compounds.

However, artificial neural network methods may improve both accuracy and a speed of calculations but still have difficulties in constructing a training set for learning intra- and inter-molecular interactions. Specifically, conventional artificial neural network methods exhibit relatively less prediction accuracy by mainly dealing with unitary materials containing only one type of element without leaning inter-atomic forces and also, low calculation efficiency by utilizing only a central processing unit (CPU), and in addition, energy prediction accuracy significantly decreases, as learning data decrease, and an enormous computational cost is required for securing sufficient density functional theory (DFT) data.

In addition, the conventional artificial neural network methods may not extrapolate potential energy due to inability of learning physical information and also, not well predict energy of chemical reactions such as bond breaking due to poor generalization performance for unlearned structures and accordingly, are not suitable for simulations such as electrolyte decomposition reactions and the like.

SUMMARY

One aspect of the present disclosure may provide a method for predicting a potential energy of a multicomponent material by using a physics-informed artificial neural network (PINN) technology by predicting the potential energy through extrapolation, while using less learning data, and calculating energy of various structures not included in the learning data in order to learn and predict an efficient potential energy and force for a multicomponent material including an organic material and thus to achieve efficiency of a computational simulation of the organic material.

A method for predicting a potential energy of a multicomponent material according to one aspect includes encoding a structural information of a multicomponent material in which eigenvector values for each element are calculated using an atom-centered symmetry function (ACSF) of a structural information of atoms constituting the multicomponent material; calculating a bond order potential (BOP) parameter for each element using the calculated eigenvector value as an input value and using a different artificial neural network model for each type of atom to construct a physics-informed artificial neural network (PINN) model; calculating a bond order potential value for each element to construct a potential energy surface (PES); and performing structural optimization or physical property prediction of the multicomponent material using a potential energy surface.

The encoding of the structural information of the multicomponent material may include searching for atoms within a distance $r_{cut}$ (about 5 Å or less) from each atom in a three-dimensional atomic structure of the multicomponent material; calculating a distance and angle between the atoms; and calculating eigenvector values for each atom using the distance and angle between atoms as input values and using an atom-centered symmetry function (ACSF).

The atom-centered symmetry function (ACSF) may be represented by Equation 1 or Equation 2.

$$G_i^{II,Z} = \sum_{j \in N_i^Z} e^{-\eta (r_{ij}-r_s)^2/r_c^2} f_c(r_{ij}) \quad \text{[Equation 1]}$$

In Equation 1, $r_{ij}$ is a distance between atom i and atom j, $r_c$ is a cut-off radius ($r_{cut}$) to limit an influence on the center atom, $\eta$ is a variable that controls a reformation of a graph, $N_i^Z$ is a set of atoms with atomic number z among neighbor atoms of atom i, and $f_c$ is a cut-off function and is represented by Equation 3, $$G_i^{IV,Z_1,Z_2} = 2^{1-\zeta} \sum_{k \in N_i^{Z_2}} \sum_{j \in N_i^{Z_1}} (1 + \lambda \cos\theta_{ijk})^{\zeta} \cdot e^{-\eta\left(r_{ij}^2 + r_{ik}^2 + r_{jk}^2\right)/r_c^2} f_c(r_{ij}) f_c(r_{ik}) f_c(r_{jk}) \quad \text{[Equation 2]}$$

In Equation 2, $r_{ij}$ is a distance between atom i and atom j, $r_{ik}$ is a distance between atom i and atom k, $r_{jk}$ is a distance between atom j and atom k, $\theta_{ijk}$ is an angle between atom i, atom j, and atom k, is a cut-off radius ($r_{cut}$) to limit an influence on the center atom, $\eta$, $\lambda$, and $\zeta$ are variables that control a reformation of a graph, $N_i^{Z1}$ is a set of atoms with atomic number $z_1$ among neighbor atoms of atom i, $N_i^{Z2}$ is a set of atoms with atomic number $z_2$ among neighbor atoms of atom i, and $f_c$ is a cut-off function and is represented by Equation 3.

$$\text{when } r \neq r_c, \quad f_c = 0.5\left(1 + \cos\left(\pi \frac{r}{r_c}\right)\right) \quad \text{when } r > r_c, \quad f_c = 0 \quad \text{[Equation 3]}$$

In Equation 3, r is a radius of the neighbor atom from a center atom, and $r_c$ is a cut-off radius ($r_{cut}$) to limit an influence on a center atom.

The bond order potential value for each element is represented by Equation 4.

$$p_i = (A_i, \alpha_i, B_i, \beta_i, a_i, \sigma_i, h_i, \lambda_i) \quad \text{[Equation 4]}$$

In Equation 4, $A_i$, $\alpha_i$, $B_i$, $\beta_i$, $a_i$, $\sigma_i$, $h_i$, and $\lambda_i$ are one of bond order potential parameters.

For artificial neural network models different for each element, the artificial neural network parameter may be optimized by applying backpropagation to a loss function represented by Equation 5.

$$\text{Loss function (L)} = \text{error in potential energy value} + \text{error in force value} \quad \text{[Equation 5]}$$

In Equation 5, the error in the potential energy value is a difference between the potential energy value calculated by the artificial neural network using a bond order potential model and a potential energy value of learning data, the error of the force value is a difference between a force value calculated by the artificial neural network using a bond order potential model and a force value of a learning data, the potential energy value of the bond order potential model is calculated using Equation 6, and the force value of the bond order potential model is calculated using Equation 7.

$$E = \sum_i^n E_i \quad \text{[Equation 6]}$$

In Equation 6, $E_i$ is a potential energy value for each atom, and is calculated by Equation 8.

$$F = -\nabla_R E \quad \text{[Equation 7]}$$

In Equation 7, E is a total potential energy value of the multicomponent material, and $\nabla_R$ is a gradient of the potential energy E with respect to the position R of the atom.

$$E_i = \frac{1}{2} \sum_{j \neq i} \left[ e^{A_i - \alpha_i r_{ij}} - S_{ij} b_{ij} e^{B_i - \beta_i r_{ij}} \right] f_c(r_{ij}) + E_i^{(p)} \quad \text{[Equation 8]}$$

In Equation 8, $r_{ij}$ is a distance between atom i and atom j, $S_{ij}$ is calculated by Equation 9, $b_{ij}$ is calculated by Equation 11, $E_i^{(p)}$ is calculated by Equation 13, $f_c$ is a cut-off function and represented by Equation 3, and $A_i$, $\alpha_i$, $B_i$, and $\beta_i$ are one of the bond order potential parameters.

$$S_{ij} = \prod_{k \neq i,j} S_{ijk} \quad \text{[Equation 9]}$$

In Equation 9, $S_{ijk}$ is calculated by Equation 10.

$$S_{ijk} = 1 - f_c(r_{ik} + r_{jk} - r_{ij}) e^{-\lambda_i^2 \left(r_{ik} + r_{jk} - r_{ij}\right)} \quad \text{[Equation 10]}$$

In Equation 10, $f_c$ is a cut-off function and represented by Equation 3, $r_{ij}$ is a distance between atom i and atom j, $r_{ik}$ is a distance between atom i and atom k, $r_{jk}$ is a distance between atom j and atom k, and $\lambda_i$ is one of the bond order potential parameters.

$$b_{ij} = (1 + z_{ij})^{-1/2} \quad \text{[Equation 11]}$$

In Equation 11, $z_{ij}$ is calculated by Equation 12.

$$z_{ij} = a_i^2 \sum_{k \neq i,j} S_{ik} (\cos\theta_{ijk} + h_i)^2 f_c(r_{ik}) \quad \text{[Equation 12]}$$

In Equation 12, $a_i$ and $h_i$ are one of the bond order potential parameters, $\theta_{ijk}$ is an angle between atom i, atom j, and atom k, $f_c$ is a cut-off function and represented by Equation 3, and $r_{ik}$ is a distance between atom i and atom k.

$$E_i^{(p)} = -\sigma_i \left( \sum_{j \neq i} S_{ij} b_{ij} f_c(r_{ij}) \right)^{1/2} \quad \text{[Equation 13]}$$

In Equation 13, $\sigma_i$ is one of the bond order potential parameters, $f_c$ is a cut-off function and represented by Equation 3, and $r_{ij}$ is a distance between atom i and atom j.

$$\text{when } r \neq r_c,\quad f_c = 0.5\left(1+\cos\left(\pi\frac{r}{r_c}\right)\right) \qquad \text{[Equation 3]}$$
$$\text{when } r > r_c,\quad f_c = 0$$

In Equation 3, r is a radius of a neighbor atom from a center atom, and $r_c$ is a cut-off radius to limit an influence on a center atom.

In Equation 5, a ratio of the error in the potential energy value and the error in the force value is about 1:10 to about 1:100.

Before learning the artificial neural network, a single bond order potential global parameter ($p^{0,s}$) may be optimized for the entire learning data, the artificial neural network may calculate the local perturbation ($\delta p_i$) for each element, and the bond order potential (BOP) parameter may be calculated by Equation 14.

$$p_i^s = p^{0,s} + \delta p_i^s \qquad \text{[Equation 14]}$$

In Equation 14, $p^{0,s}$ is a bond order potential global parameter for each atom(s), and $\delta p_i$ is a local perturbation, and is calculated by Equation 15.

$$\delta p_i = \theta_0 MLP^s(G_i) \quad (\theta_0 \in \mathbb{R}^8) \qquad \text{[Equation 15]}$$

In Equation 15, $MLP^s$ $(G_i)$ is a value calculated from an artificial neural network model for each element type (s) when the input value $G_i$ is input, and $\theta_0$ is a learning scaling factor.

The global parameter ($p^{0,s}$) may include 8 real values and may be initialized to a random value and then optimized using Adam or BFGS (Broyden-Fletcher-Goldfarb-Shanno).

The learning scaling factor ($\theta_0$) may include 8 real values, initial values of all 8 may be 1.0, and the learning scale factor ($\theta_0$) may also be learned by inputting it as an input value to the artificial neural network model.

The constructing of the potential energy surface may be performed by, using the bond order potential (BOP) parameter for each element, calculating the potential energy value using Equation 6, and calculating the force value using Equation 7.

The method for predicting a potential energy of a multicomponent material according to one aspect uses the physics-informed artificial neural network (PINN) to predict the potential energy through extrapolation, while using less learning data, and calculate energy of various structures not included in the learning data and thereby, learn and predict an efficient potential energy and force for a multicomponent material including an organic material and resultantly, achieve efficiency of a computational simulation of the organic material.

DETAILED DESCRIPTION

Figure 1:
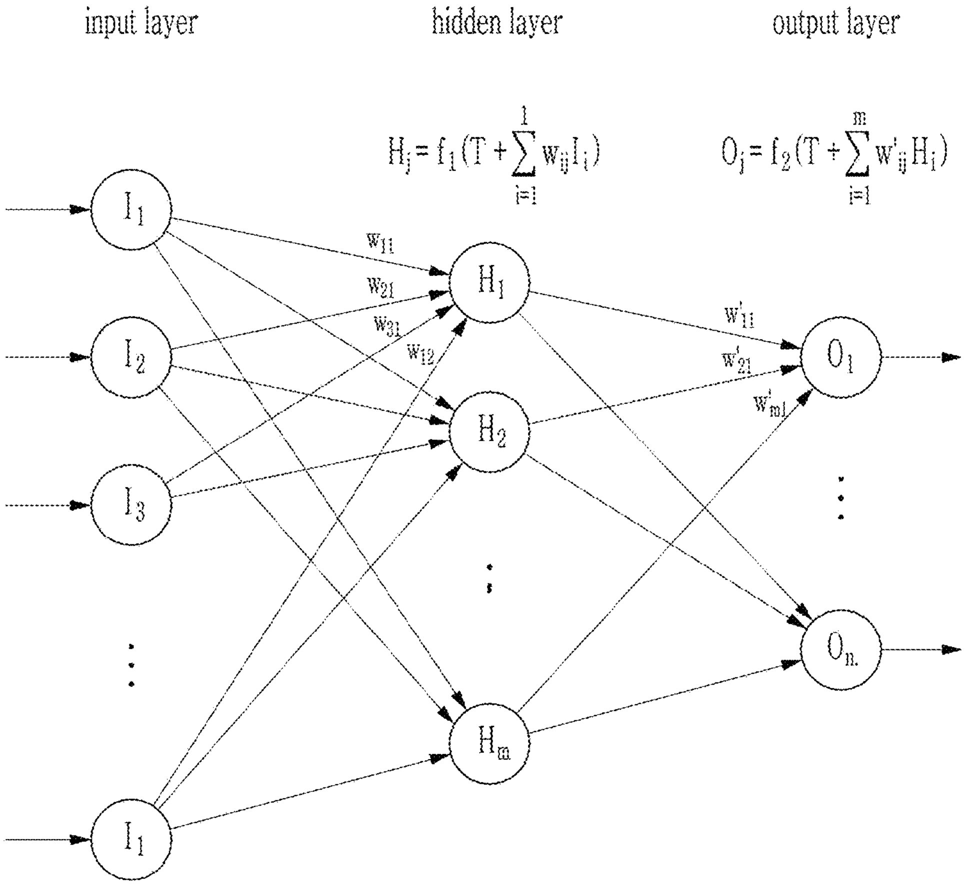
FIG. 1 is a view showing an example of an artificial neural network.

The advantages, features, and aspects to be described hereinafter will become apparent from the following description of the embodiments with reference to the accompanying drawings, which is set forth hereinafter. However, the present disclosure may be not limited to embodiments that are described herein. Unless otherwise defined, all terms (including technical and scientific terms) used in this specification may be used with meanings that can be commonly understood by those skilled in the art. The terms defined in a generally-used dictionary may not be interpreted ideally or exaggeratedly unless clearly defined. Throughout the specification and claims which follow, unless explicitly described to the contrary, the word “comprise/include” or variations such as “comprises/includes” or “comprising/including” will be understood to imply the inclusion of stated elements but not the exclusion or any other elements.

Each block in the attached block diagram and each step in the flow diagram may be combined by computer program instructions (execution engine), and since these computer program instructions may be loaded in a processor of a general computer, a special-purpose computer, or other programmable data-processing devices, the instructions executed by the processor in the computers or other programmable data-processing devices may produce a means of performing the functions described in each block of the block diagram or each step of in the flow diagram.

Since these computer program instructions may also be stored in a computer-usable or computer-readable memory that may be directed to the computers or other programmable data-processing devices to implement the functions in a specific manner, the instructions stored in the computer-usable or computer-readable memory may produce a manufactured article containing the instruction means performing the functions described in each block of the block diagram or each step of in the flow diagram.

In addition, since these computer program instructions may be loaded on the computers or other programmable data-processing devices to perform a series of operational steps in the computers or other programmable data-processing devices and produce a computer-executable process, the instructions executing the computers or other programmable data-processing devices may provide steps for executing the functions described in each block of the block diagram or each step of in the flow diagram.

In addition, each block or each step may represent a portion of module, segment, or code containing one or more executable instructions for executing specified logical functions, but in some alternative embodiments, it should be noted that the functions mentioned in the blocks and the steps may occur out of order. For example, two blocks or steps shown in succession may be substantially simultaneously performed, and in addition, the blocks or steps may be performed in reverse order of the corresponding functions, if necessary.

Hereinafter, an embodiment according to this aspect will be described in detail with reference to the accompanying drawings. However, the embodiment of this aspect illustrated below may be modified into various other forms, wherein a scope of this aspect is not limited to the following examples.

Figure 2:
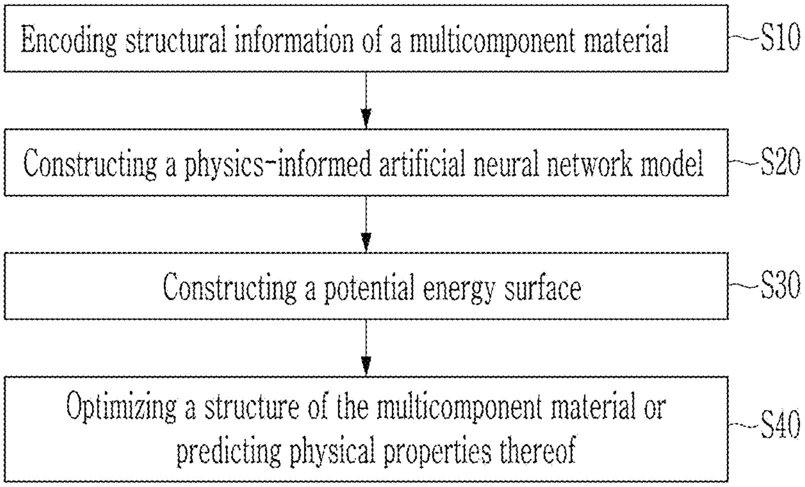
FIG. 2 is a flowchart showing a method for predicting a potential energy of a multicomponent material according to one aspect.

FIG. 2 is a flowchart showing a method for predicting a potential energy of a multicomponent material according to one aspect. Hereinafter, a method for predicting a potential energy of a multicomponent material will be described in detail with reference to FIG. 2.

The method for predicting a potential energy of a multicomponent material includes a step of encoding structural information of a multicomponent material (S10), a step of constructing a physics-informed artificial neural network (PINN) model (S20), a step of constructing a potential energy surface (PES) (S30), and a step of optimizing the structure of the multicomponent material or predicting physical properties thereof (S40).

In the structural information encoding step (S10) of the multicomponent material, eigenvector values for each element are calculated using the structural information of the atoms constituting the multicomponent material using the atom center symmetry function (ACSF).

The structural information encoding step (S10) of the multicomponent material, when given with a three-dimensional atomic structure, is a process of expressing information about positions and types of atoms inside the corresponding structure as an eigenvector.

For example, in the structural information encoding step (S10) of the multicomponent material, the eigenvector of each atom may be calculated by searching for atoms within a distance $r_{cut}$ from each atom in the three-dimensional atomic structure of the multicomponent material, calculating an interatomic distance, an angle, and a type of neighbor atoms, and using the interatomic distance and the angle as input values and an atom-centered symmetry function (ACSF) for each surrounding atom type. Herein, $r_{cut}$ may be, for example, less than or equal to about 5 Å or about 4 Å to about 5 Å.

Since energy of the structure is invariant to rotational, symmetric, or translational transformations in space, the structural information encoding also uses the atom-centered symmetry function (ACSF) to express the structure energy as a quantity invariant to these transformations.

Through the atom-centered symmetry function (ACSF), the information about a distance or an angle with the neighbor atoms may be expressed as a high-dimensional vector, and an chemical environment of the multicomponent material also may be effectively simulated by organizing structural information according to types of atoms into different components within the vector.

For example, the atom-centered symmetry function may be expressed by Equation 1 or Equation 2.

$$G_i^{II,Z} = \sum_{j \in N_i^Z} e^{-\eta (r_{ij} - r_s)^2 / r_c^2} f_c(r_{ij}) \quad \text{[Equation 1]}$$

In Equation 1, $r_{ij}$ is a distance between atom i and atom j, $r_c$ is a cut-off radius ($r_{cut}$) to limit an influence on a center atom, η are variables that control a reformation of a graph, $N_i^Z$ is a set of atoms with atomic number z among neighbor atoms of atom i, and $f_c$ is a cut-off function and represented by Equation 3.

For example, when atoms with atomic numbers 2 and 3 exist around an atom with atomic number i=1, Ni={2, 3}, and the eigenvector values $G_1^{II,2}$ and $G_i^{II,3}$ for atomic number i=1 can be obtained.

$$G_i^{IV,Z_1,Z_2} = 2^{1-\zeta} \sum_{k \in N_i^{Z_2}} \sum_{j \in N_i^{Z_1}} (1 + \lambda \cos\theta_{ijk})^{\zeta} \cdot e^{-\eta (r_{ij}^2 + r_{ik}^2 + r_{jk}^2)/r_c^2} f_c(r_{ij}) f_c(r_{ik}) f_c(r_{jk}) \quad \text{[Equation 2]}$$

In Equation 2, $r_{ij}$ is a distance between atom i and atom j, $r_{ik}$ is a distance between atom i and atom k, $r_{jk}$ is a distance between atom j and atom k, $\theta_{ijk}$ is an angle between atom i, atom j, and atom k, $r_c$ is a cut-off radius to limit an influence on a center atom, η, λ, and ζ are variables that control a reformation of a graph, $N_i^{Z1}$ is a set of atoms with atomic number $z_1$ among neighbor atoms of atom i, $N_i^{Z2}$ is a set of atoms with atomic number $z_2$ among neighbor atoms of atom i, and $f_c$ is a cut-off function and is represented by Equation 3.

$$\text{when } r \neq r_c, \quad f_c = 0.5\left(1 + \cos\left(\pi \frac{r}{r_c}\right)\right) \quad \text{when } r > r_c,\ f_c = 0 \quad \text{[Equation 3]}$$

In Equation 3, r is a radius of a neighbor atom from a center atom, $r_c$ is a cut-off radius to limit an influence on a center atom.

This atom-centered symmetry function (ACSF) may output a constant value, even though the neighbor atom rotates or moves relative to the central atom in the three-dimensional structure. For example, Table 1 shows input values in a moving model or a rotational model by using the atom-centered symmetry function (ACSF) expressed by Equation 1.

TABLE 1

| | η | Reference placement | Moving model | Rotation model |
|---|---|---|---|---|
| Cartesian coordinate system | None | 8, 8 | 9, 4 | 3, 8 |
| Symmetric function transformation | 0.05 | 0.122 | 0.122 | 0.122 |
| | 2 | 0.038 | 0.038 | 0.038 |
| | 4 | 0.011 | 0.011 | 0.011 |
| | 8 | 0.001 | 0.001 | 0.001 |

However, when the input values defined by the atom-centered symmetry function (ACSF) are expressed only as scalar values, there may be a problem that the same values are output in different batches. In other words, the arrangements around the atom may not be expressed as eigenvalues.

In order to solve this problem, the atom arrangements are converted into vectors rather than the scalar values, creating an array of eigenvalues according to each of the structure arrangements. In other words, in the atom-centered symmetry function (ACSF) of Equation 1, η may be changed to obtain an eigenvector value for one atom arrangement.

For example, Table 2 shows eigenvector values for cases that $r_{ij}$ is 1, 2, and 4, while η is changed into 0.05, 2, 4, 8, 20, 40, and 80.

TABLE 2

| | | $r_{ij}$ | | |
|---|---|---|---|---|
| | η | 1 | 2 | 4 |
| Scalar value | 80 | 0.142 | 4e−04 | 2.2e−14 |
| Eigenvector | 80 | 0.142 | 4e−04 | 2.2e−14 |
| value | 40 | 0.366 | 0.018 | 8.5e−08 |
| | 20 | 0.587 | 0.118 | 1.7e−04 |
| | 8 | 0.780 | 0.368 | 0.016 |
| | 4 | 0.858 | 0.537 | 0.071 |
| | 2 | 0.899 | 0.649 | 0.151 |
| | 0.05 | 0.942 | 0.780 | 0.317 |

Referring to Table 2, when only the scalar values are output depending on a structure, a case that $r_{ij}$ is 1 is distinguished from another case that $r_{ij}$ is 2, but the case that $r_{ij}$ is 2 is similar to a case that $r_{ij}$ is 4, which may not be distinguished each other. In other words, similar (the same) values may be output, even though the structures are different.

Accordingly, when the values obtained by changing η in the atom-centered symmetry function (ACSF) of Equation 1 are converted into eigenvector values for one atom arrangement, the eigenvector values according to the structures may be used as input values of the artificial neural network.

In addition, in Equation 2, a Gaussian-type symmetric function may be obtained by changing η, λ, and/or ζ, and eigenvector values according to a combination of η, λ, and/or ζ also may be used as input values of the artificial neural network.

In Equation 1, a symmetric function η and in Equation 2, any combination of the symmetric function η, λ, and/or ζ may be used as input nodes. Accordingly, the actual number of the input nodes may use the entire eigenvector values calculated through Equation 1 or Equation 2 as input values. For example, when n eigenvector values in Equation 1 and m eigenvector values in Equation 2 are calculated, m+n eigenvector values in total may be input values.

In the step (S20) of constructing a physics-informed artificial neural network (PINN) model, the calculated eigenvector values are used as input values, and a different artificial neural network model for each element may be used to calculate a bond order potential (BOP) parameter for each element to construct the physics-informed artificial neural network (PINN) model.

The method for predicting a potential energy of a multi-component material according to this aspect uses a different artificial neural network model for each element to predict a different bond order potential (BOP) parameter when it has the same geometric structure but different types of elements. Accordingly, a potential energy prediction model even for materials composed of various types of elements may be developed.

The step (S20) of constructing the physics-informed artificial neural network (PINN) model is a process of learning local bond order potential (BOP) parameters for each atom in the structure by using an artificial neural network model with the encoded structural information as input values.

Optionally, before training the artificial neural network, a normalization process of learning parameters through global fitting the bond order potential (BOP) parameter set for each element may be performed.

For example, the normalization process of the learning parameters may be performed by optimizing a single bond order potential global parameter (global parameter, $p^{0,s}$) for the entire learning data before training the artificial neural network, wherein the artificial neural network may calculate local perturbation ($\delta p_i$) for each element.

Herein, the bond order potential (BOP) parameters for each element may be calculated according to Equation 14.

$$p_i^s = p^{0,s} + \delta p_i^s \qquad \text{[Equation 14]}$$

In Equation 14, $p^{0,s}$ is a bond order potential global parameter for each atom (s) and includes eight real numbers. $p^{0,s}$ may be, for example, initialized by a random value and then, optimized by an optimization program such as Adam or BFGS (Broyden-Fletcher-Goldfarb-Shanno). One global parameter ($p^{0,s}$) is respectively prepared for each atom.

$\delta p_i$ is a local perturbation value, which is calculated by Equation 15.

$$\delta p_i = \theta_0\, MLP^s(G_i)\ (\theta_0 \in R^8) \qquad \text{[Equation 15]}$$

In Equation 15, $MLP^s$, which is an abbreviation for multilayer perceptron, is calculated from an artificial neural network model for each element type (s) when an input value $G_i$ is input, Oo is a scaling factor, and eight real numbers are included ($\theta_0 \in R^8$). In other words, a local perturbation factor ($\delta p_i$) may be obtained by multiplying a value calculated from the artificial neural network model for each element type (s) by the scaling factor ($\theta_0$).

Since the chemical structure is not very diverse, after determining a global parameter ($p^{0,s}$) as a base line, a deviation from the global parameter ($p^{0,s}$) is calculated by using the artificial neural network model to accelerate the learning.

In addition, since each parameter ($A_i$, $\alpha_i$, $B_i$, $\beta_i$, $a_i$, $\sigma_i$, $h_i$, and $\lambda_i$, as described later) has different value ranges in the bond order potential (BOP) parameter, the learning may be accelerated by the scaling factor ($\theta_0$). The scaling factor ($\theta_0$) may have an initial value of 1.0 in all 8 parameters, wherein the scaling factor ($\theta_0$) may also be learned by inputting it as an input value into the artificial neural network model.

Figure 3:
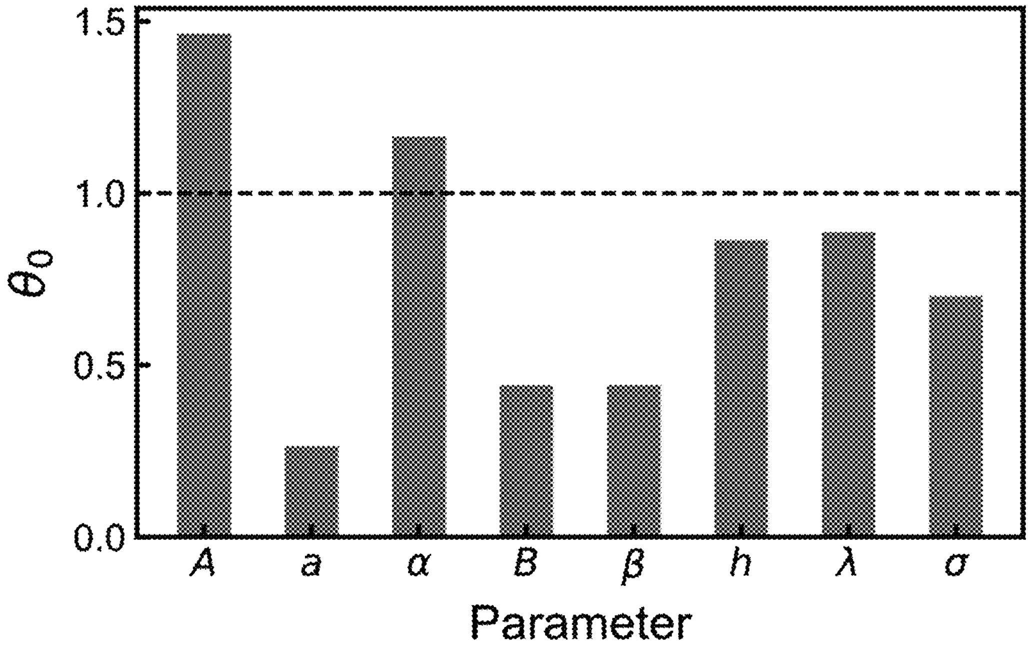
FIG. 3 is a graph showing the learning scaling factor ($\theta_0$) learned through a physics-informed artificial neural network (PINN) model.
Figure 4:
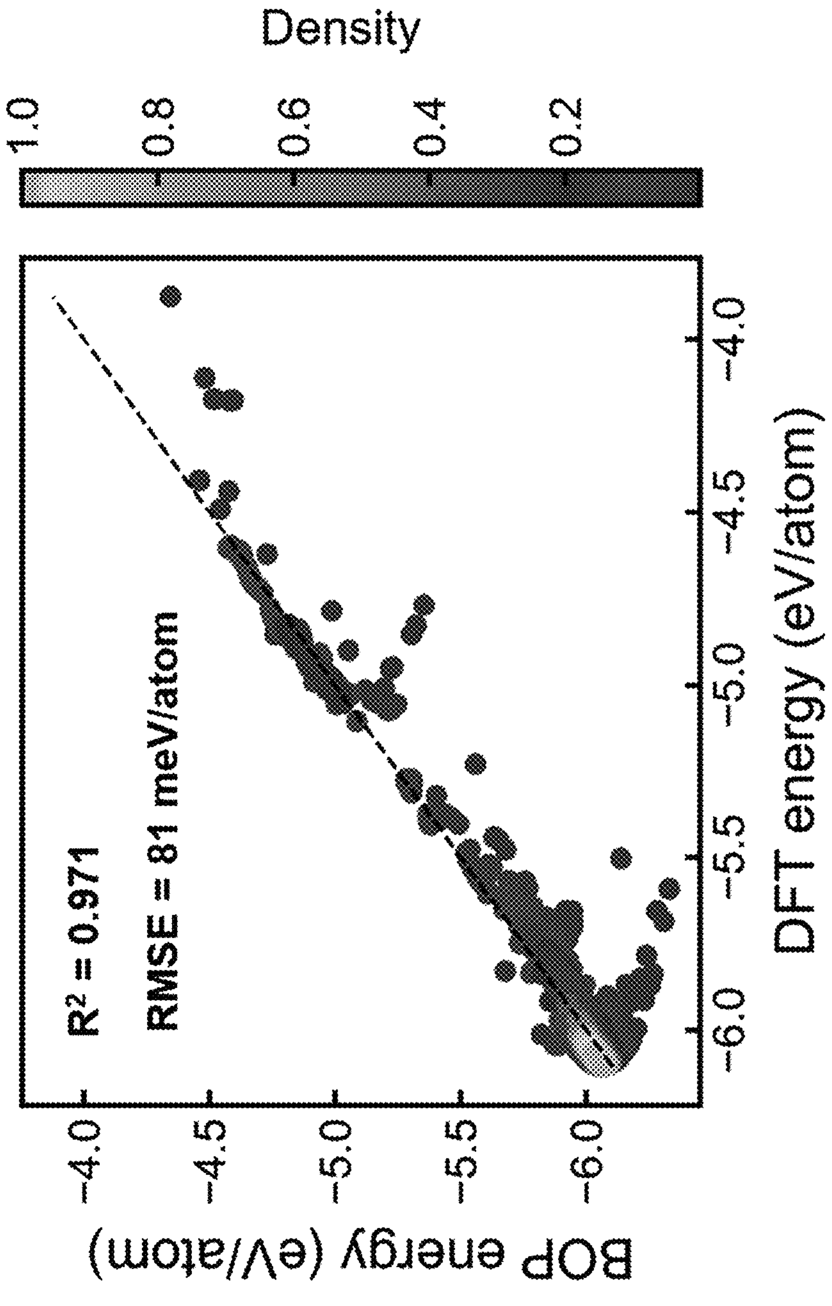
FIG. 4 is a graph showing the results of fitting global parameters.

FIG. 3 is a graph showing an example of the scaling factor ($\theta_0$) learned through the physics-informed artificial neural network (PINN) model, and FIG. 4 is a graph showing an example of the results obtained by fitting the global parameters. Referring to FIGS. 3 and 4, the learning may be accelerated by optimizing the single bond order potential (BOP) parameter set ($p^{0,s}$) for the premise learning data before training the artificial neural network, and the learnable scaling factor ($\theta_0$) for each parameter may be introduced to effectively calculate the different ranges per each bond order potential (BOP) parameter.

Figure 5:
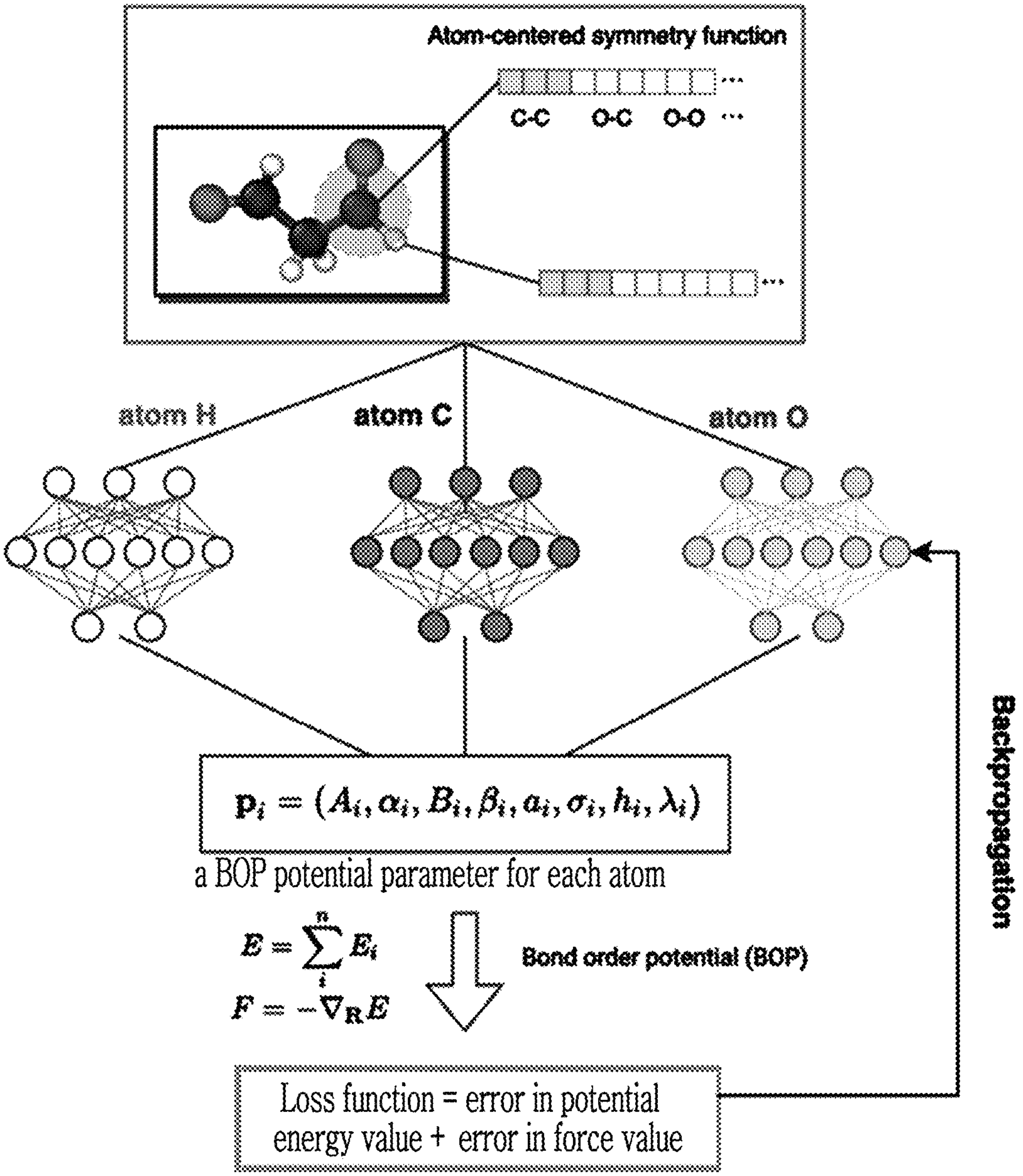
FIG. 5 is a view schematically showing a physics-informed artificial neural network (PINN) model.

FIG. 5 is a graph schematically showing the physics-informed artificial neural network (PINN) model. Referring to FIG. 5, the physics-informed artificial neural network (PINN) model does not directly calculate energy through the artificial neural network but calculates a local bond order potential (BOP) potential parameter corresponding to each atom.

In other words, each bond order potential (BOP) parameter is calculated by constructing a different artificial neural network model for each center atom and using an independent rule for each element. Referring to FIG. 5, the artificial neural network model may include each artificial neural network model for a hydrogen (H) atom, a carbon (C) atom, and an oxygen (O) atom.

In addition, in order to effectively learn a ratio of each parameter in the bond order potential (BOP) parameter set, the learnable scaling factor ($\theta_0$), a weight for each parameter, is used.

However, as described above, when the global parameter ($p^{0,s}$) is used, the artificial neural network model may not directly learn the bond order potential (BOP) parameter but learn the local perturbation ($\delta p_i$), wherein the bond order potential (BOP) parameter may be obtained according to Equation 14.

For example, an bond order potential parameter for each element may be expressed by Equation 4.

$$p_i = (A_i, \alpha_i, B_i, \beta_i, a_i, \sigma_i, h_i, \lambda_i) \qquad \text{[Equation 4]}$$

In Equation 4, $A_i$, $\alpha_i$, $B_i$, $\beta_i$, $a_i$, $\sigma_i$, $h_i$, and $\lambda_i$ is one of bond order potential parameters, which are used to calculate a bond order potential of Equation 8.

For example, a different artificial neural network model for each element may be to optimize an artificial neural network parameter by applying a backpropagation algorithm to a loss function represented by Equation 5.

$$\text{Loss function } (L) = \text{error in potential energy value} + \text{error in force value} \qquad \text{[Equation 5]}$$

In Equation 5, the error in the potential energy value is a difference between the potential energy value calculated by the artificial neural network using a bond order potential model and a potential energy value of learning data, and the error of the force value is a difference between a force value calculated by the artificial neural network using a bond order potential model and a force value of a learning data.

The potential energy value of the bond order potential model is calculated using Equation 6, and the force value of the bond order potential model is calculated using Equation 7.

$$E = \sum_{i}^{n} E_i \qquad \text{[Equation 6]}$$

In Equation 6, $E_i$ is a potential energy value for each atom, and is calculated by Equation 8.

$$F = -\nabla_R E \qquad \text{[Equation 7]}$$

In Equation 7, E is a total potential energy value of the multicomponent material, and $\nabla_R$ is a gradient of the potential energy E with respect to the position R of the atom.

$$E_i = \frac{1}{2}\sum_{j\neq i}\left[e^{A_i-\alpha_i r_{ij}} - S_{ij}b_{ij}e^{B_i-\beta_i r_{ij}}\right] f_c(r_{ij}) + E_i^{(p)} \qquad \text{[Equation 8]}$$

In Equation 8, $r_{ij}$ is a distance between atom i and atom j, $S_{ij}$ is calculated by Equation 9, $b_{ij}$ is calculated by Equation 11, $E_i^{(p)}$ is calculated by Equation 13, $f_c$ is a cut-off function and represented by Equation 3, and $A_i$, $\alpha_i$, $B_i$, and $\beta_i$ are one of the bond order potential parameters.

$$S_{ij} = \prod_{k\neq i,j} S_{ijk} \qquad \text{[Equation 9]}$$

In Equation 9, $S_{ijk}$ is calculated by Equation 10.

$$S_{ijk} = 1 - f_c(r_{ik} + r_{jk} - r_{ij})\, e^{-\lambda_i^2 (r_{ik}+r_{jk}-r_{ij})} \qquad \text{[Equation 10]}$$

In Equation 10, $f_c$ is a cut-off function and represented by Equation 3, $r_{ij}$ is a distance between atom i and atom j, $r_{ik}$ is a distance between atom i and atom k, $r_{jk}$ is a distance between atom j and atom k, and $\lambda_i$ is one of the bond order potential parameters.

$$b_{ij} = (1 + z_{ij})^{-1/2} \qquad \text{[Equation 11]}$$

In Equation 11, $z_{ij}$ is calculated by Equation 12.

$$z_{ij} = a_i^2 \sum_{k\neq i,j} S_{ik}\,(\cos\theta_{ijk} + h_i)^2 f_c(r_{ik}) \qquad \text{[Equation 12]}$$

In Equation 12, $a_i$ and $h_i$ are one of the bond order potential parameters, $\theta_{ijk}$ is an angle between atom i, atom j, and atom k, $f_c$ is a cut-off function and represented by Equation 3, and $r_{ik}$ is a distance between atom i and atom k.

$$E_i^{(p)} = -\sigma_i\left(\sum_{j\neq i} S_{ij} b_{ij} f_c(r_{ij})\right)^{1/2} \qquad \text{[Equation 13]}$$

In Equation 13, $\sigma_i$ is one of the bond order potential parameters, $f_c$ is a cut-off function and represented by Equation 3, and $r_{ij}$ is a distance between atom i and atom j.

$$\text{when } r \neq r_c,\quad f_c = 0.5\left(1 + \cos\left(\pi\frac{r}{r_c}\right)\right) \qquad \text{[Equation 3]}$$

$$\text{when } r > r_c,\ f_c = 0$$

In Equation 3, r is a radius of a neighbor atom from a center atom, and $r_c$ is a cut-off radius to limit an influence on a center atom.

In Equation 5, a ratio of the error in the potential energy value and the error in the force value may be about 1:10 to about 1:100. In other words, the loss function may be obtained by multiplying the error in the potential energy value by 1.0 and multiplying the error in the force value by 10 to 100 and then, adding them up. When the error in the force value is more weighted than the error in the potential energy value, the artificial neural network may be more quickly and accurately learned.

In the step (S30) of constructing the potential energy surface (PES), the potential energy surface (PES) may be constructed by calculating a bond order potential for each element.

In other words, the step (S30) of constructing the potential energy surface (PES) is a process of calculating structure energy by the bond order potential (BOP) by using a bond order potential (BOP) parameter obtained through the physics-informed artificial neural network (PINN) model.

For example, the step (S30) of constructing the potential energy surface (PES) may be performed by using the bond order potential (BOP) parameter for each element to calculate a potential energy value according to Equation 6 and calculate a force value according to Equation 7.

All the processes are accelerated through a graphic processing unit (GPU), which may be about 300 times faster than quantum physics, wherein computation of the graphic processing unit (GPU) may be accelerated through full differentiable programming, which makes it possible to overcome the limitations of the conventional unitary physics-informed artificial neural network potential production technology.

In the step (S40) of optimizing the structure of a multicomponent material or predicting physical properties of the multicomponent material, the potential energy surface (PES) is used to optimize the structure of a multicomponent material or predicting physical properties of the multicomponent material.

For example, the potential energy surface (PES) constructed through the aforementioned process may be applied for the structural optimization through the energy prediction, wherein a force between atoms obtained through differentiation of the potential energy surface (PES) may be used in simulations to predict various computational properties such as molecular dynamics simulations and the like.

Figure 6:
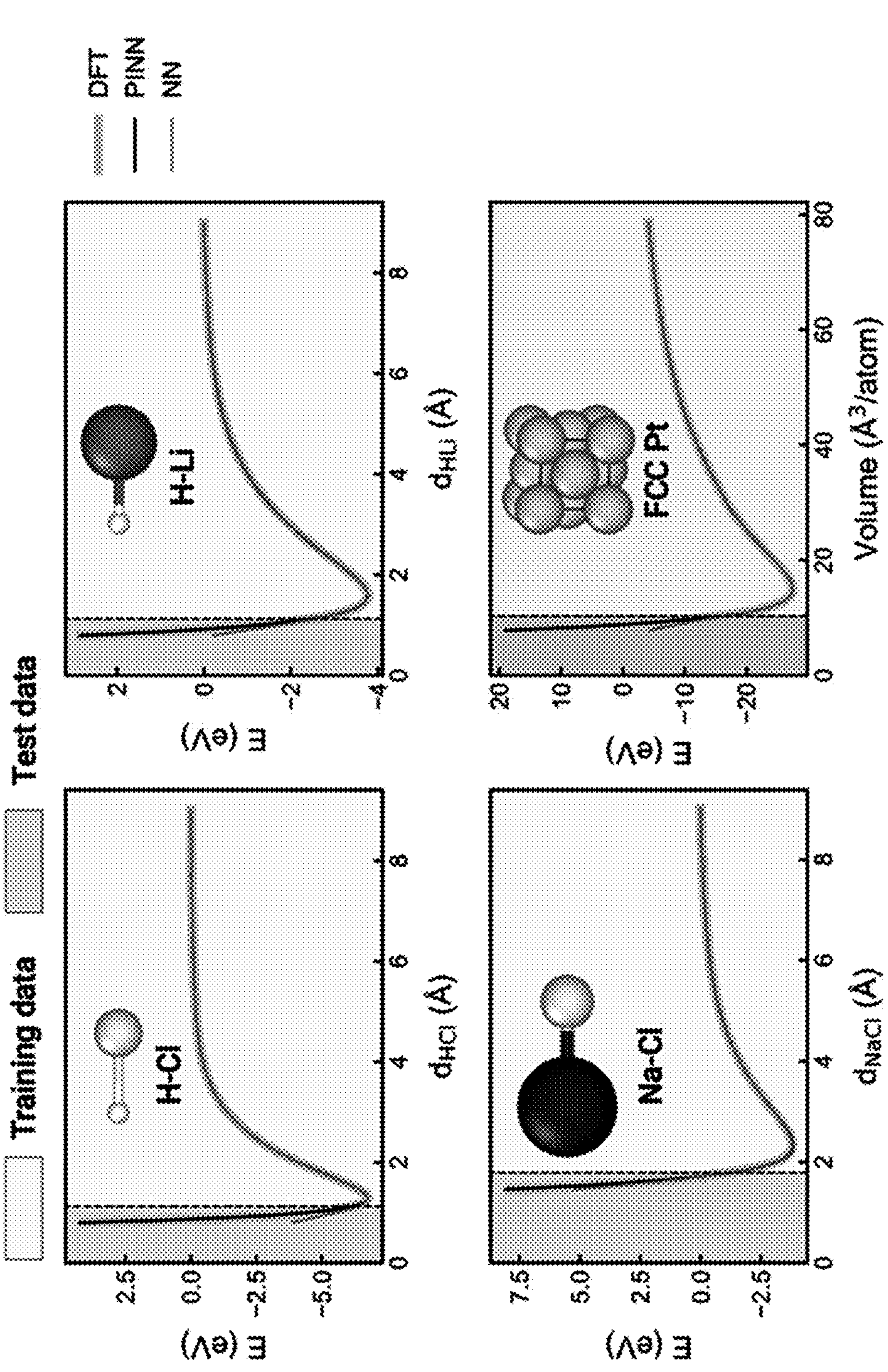
FIG. 6 is graphs showing the extrapolation performance of the physics-informed artificial neural network (PINN) model.

FIG. 6 is graphs showing extrapolation performance of the physics-informed artificial neural network (PINN) model. In FIG. 6, DFT is a case of using a density functional theory (DFT), NN is a case of using a conventional artificial neural network (NN) model, and PINN is a case of using the physics-informed artificial neural network (PINN) model according to the aspect.

Referring to FIG. 6, the physics-informed artificial neural network (PINN) model is easy to extrapolate, as the bond order potential (BOP) parameters are learned based on physical information. In other words, the physics-informed artificial neural network (PINN) model may predict energy in a structural region where repulsion rather than learning data is dominant for diatom molecules, ion bond structures, bulk metals, etc. On the contrary, the conventional artificial neural network (NN) model may not predict the energy of the structural region where the repulsion is dominant.

A rMD17 data set, which consists of first-principle molecular dynamics trajectories for organic molecules, is used as learning data to construct each potential energy surface (PES) for benzene ($C_6H_6$), malonaldehyde ($C_3H_4O_2$), salicylic acid ($C_7H_6O_3$), uracil ($C_4H_4N_2O_2$) molecules among them, and the results are shown in Table 3.

In Table 3, NN is a case of using the conventional artificial neural network (NN) model, and PINN is a case of using the physics-informed artificial neural network (PINN) model.

Figure 7:
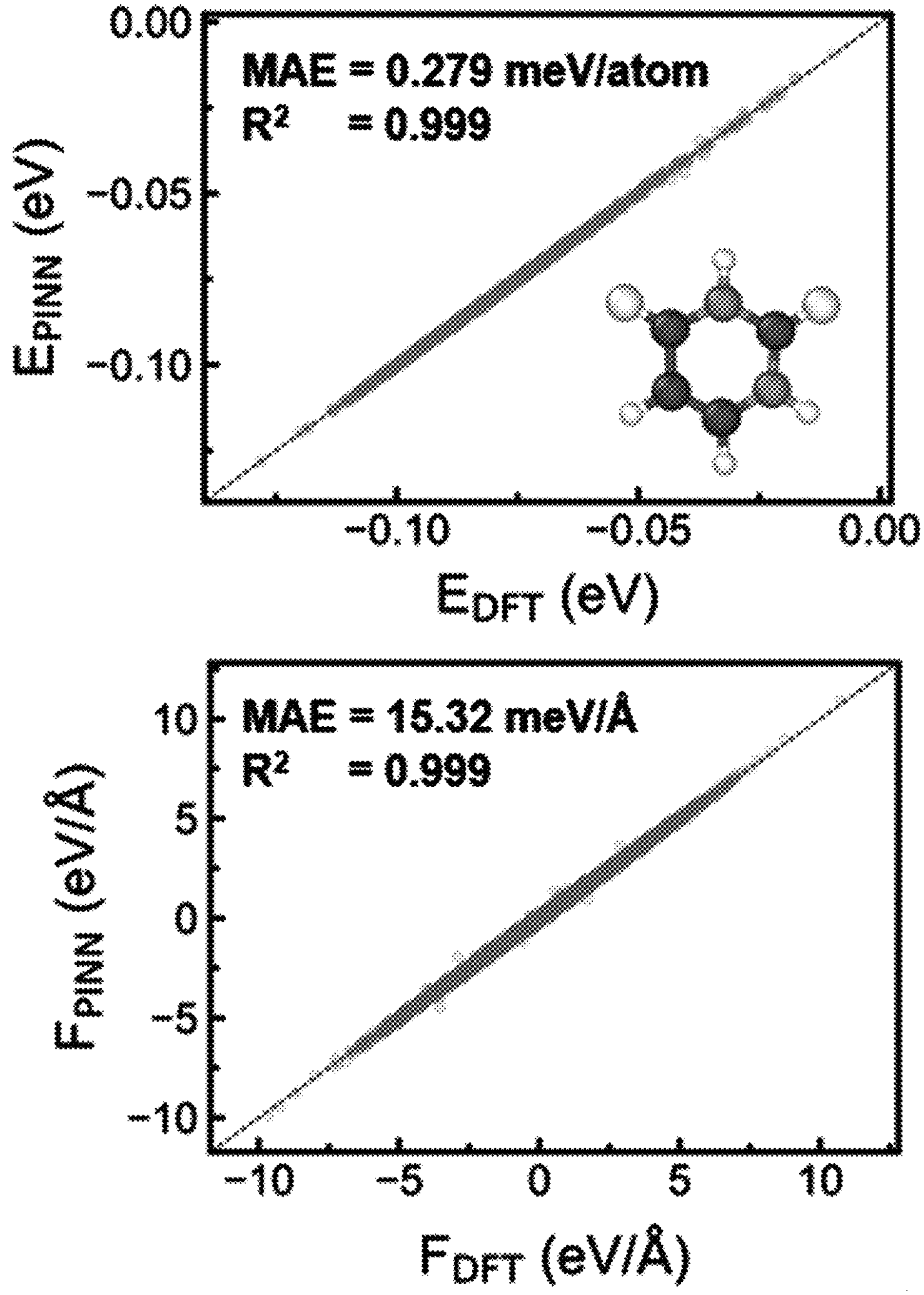
FIG. 7 is a graph showing the results of calculating the potential energy and force of uracil molecules using a physics-informed artificial neural network (PINN) model.

In addition, FIG. 7 is a graph showing the potential energy and force results of the Uracil molecules by using the physics-informed artificial neural network (PINN) model.

TABLE 3

| | Energy MAE (meV/atom) | | Force MAE (meV/Å) | |
|---|---|---|---|---|
| | NN | PINN | NN | PINN |
| Benzene | 2.072 | 0.125 | 36.44 | 12.76 |
| Malondialdehyde | 2.917 | 1.734 | 77.99 | 58.05 |
| Salicylic acid | 3.336 | 0.823 | 168.49 | 38.08 |
| Uracil | 1.870 | 0.279 | 136.41 | 15.32 |

Referring to FIGS. 1 and 7, when the physics-informed artificial neural network (PINN) model is used, even though each molecule is learned through only 1,000 structures out of about 500,000 structures in total, compared with the conventional artificial neural network (NN) model, prediction accuracy of the potential energy is at most 25 times improved, and prediction accuracy of eh force is at most 8 times improved.

A bonding length and an angle of benzene ($C_6H_6$) are calculated in various methods, and the results are shown in Table 4.

In Table 4, DFT indicates a case of using the density functional theory (DFT), and PINN indicates a case of using the physics-informed artificial neural network (PINN) according to the aspect.

Figure 8:
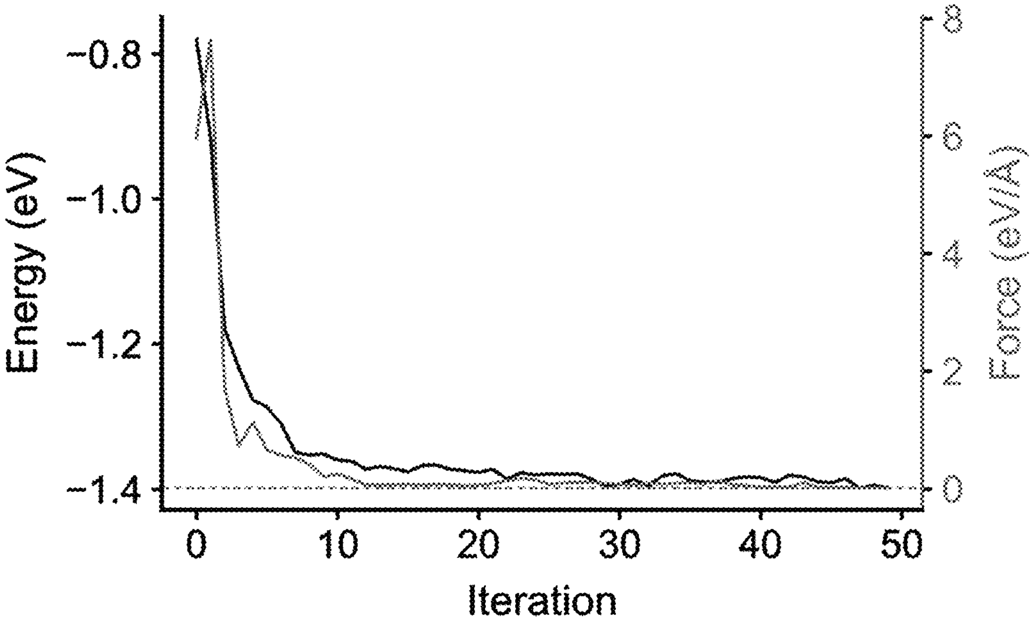
FIG. 8 is a graph showing the potential energy of benzene calculated using a physics-informed artificial neural network (PINN) model.

FIG. 8 is a graph showing the potential energy of benzene, which is calculated by using the physics-informed artificial neural network (PINN) model.

TABLE 4

| | C—C bond length (Å) | C—C—H angle (°) |
|---|---|---|
| Initial | 1.421 | 124.7 |
| Optimized (DFT) | 1.399 | 120.0 |
| Optimized (PINN) | 1.404 | 120.0 |
| Experimental | 1.39 | 120.0 |

Referring to FIGS. 4 and 8, as a result of performing a physical property prediction simulation by using the physics-informed artificial neural network (PINN) model, a bonding length may be predicted within an error of about 1% with an experimental value and also, within an error of about 1% with a case of using the density functional theory (DFT).

Figure 9:
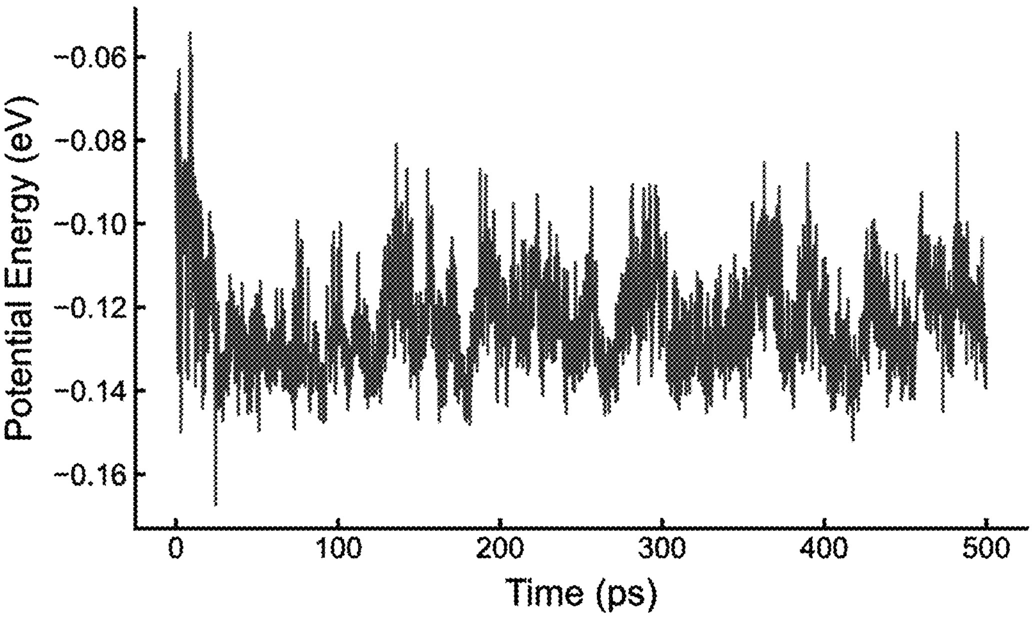
FIG. 9 is a graph showing the results of molecular dynamics simulation of ethanol using a physics-informed artificial neural network (PINN) model.

FIG. 9 is a graph showing the results of performing molecular dynamics simulation of ethanol by using the physics-informed artificial neural network (PINN) model.

In FIG. 9, computation time is 0.005 s/step (DFT: 1.67 s/step).

Referring to FIG. 9, equilibrium is maintained for 400 ps after about 100 ps.

In this way, when the learned physics-informed artificial neural network (PINN) model is used, computational material simulations such as structural optimization or molecular dynamics, etc. may be performed with the same accuracy as the density functional theory (DFT) at an about 300 times or faster speed than the density functional theory (DFT).

In addition, the learned physics-informed artificial neural network (PINN) model may be used in the molecular dynamics simulations for so long a period of time as not to be reached by the density functional theory (DFT) and stably maintain an equilibrium state.

Hereinafter, specific examples of the present disclosure are presented. However, the examples described below are only for specifically illustrating or explaining the present disclosure, and the scope of the invention is not limited thereto.

Example 1

Figure 10:
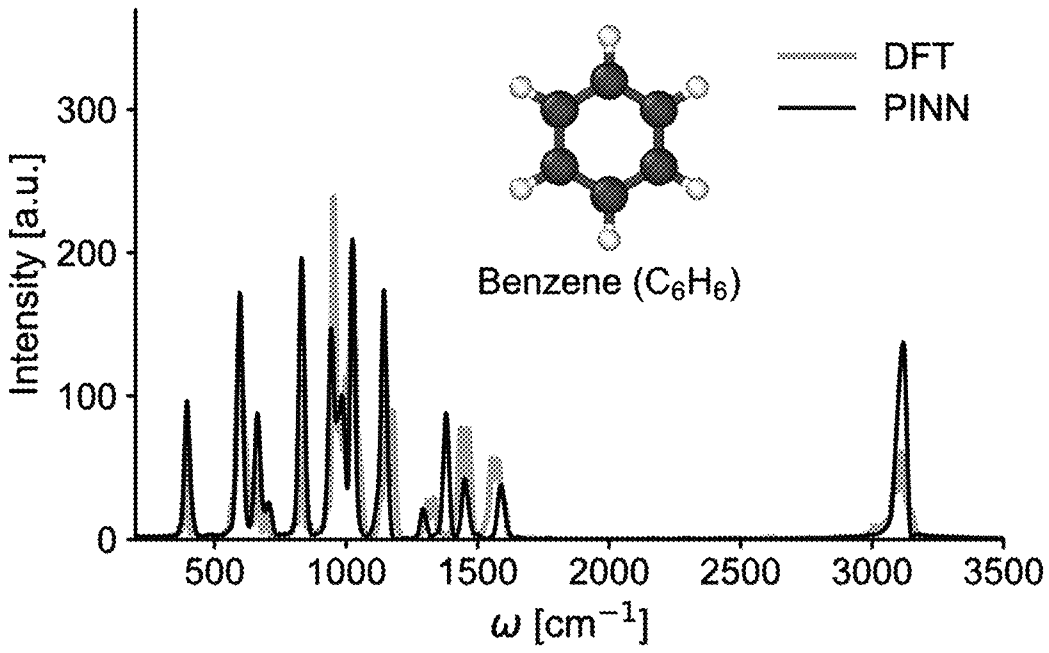
FIG. 10 is a graph showing the results of calculating the power spectrum of benzene using a physics-informed artificial neural network (PINN) model in Example 1.

FIG. 10 is a graph showing the result of calculating a power spectrum of benzene by using a physics-informed artificial neural network (PINN) model.

In FIG. 10, DFT indicates a case of using a density functional theory (DFT), and PINN indicates a case of using a physics-informed artificial neural network (PINN).

The power spectrum representing a vibration mode of molecules may be calculated by using molecular dynamics calculations, but since long-term dynamic trajectories are required to simulate various ensembles of molecular structures, the power spectrum may be efficiently calculated through a graphics processing unit (GPU) accelerated molecular dynamics simulation by using the physics-informed artificial neural network (PINN) model.

Referring to FIG. 10, when the physics-informed artificial neural network (PINN) model is used, the spectrum may be obtained through simulation of about 100 ps, from which vibration modes obtained through the density functional theory (DFT) may be predicted with high accuracy.

Example 2

Figure 11:
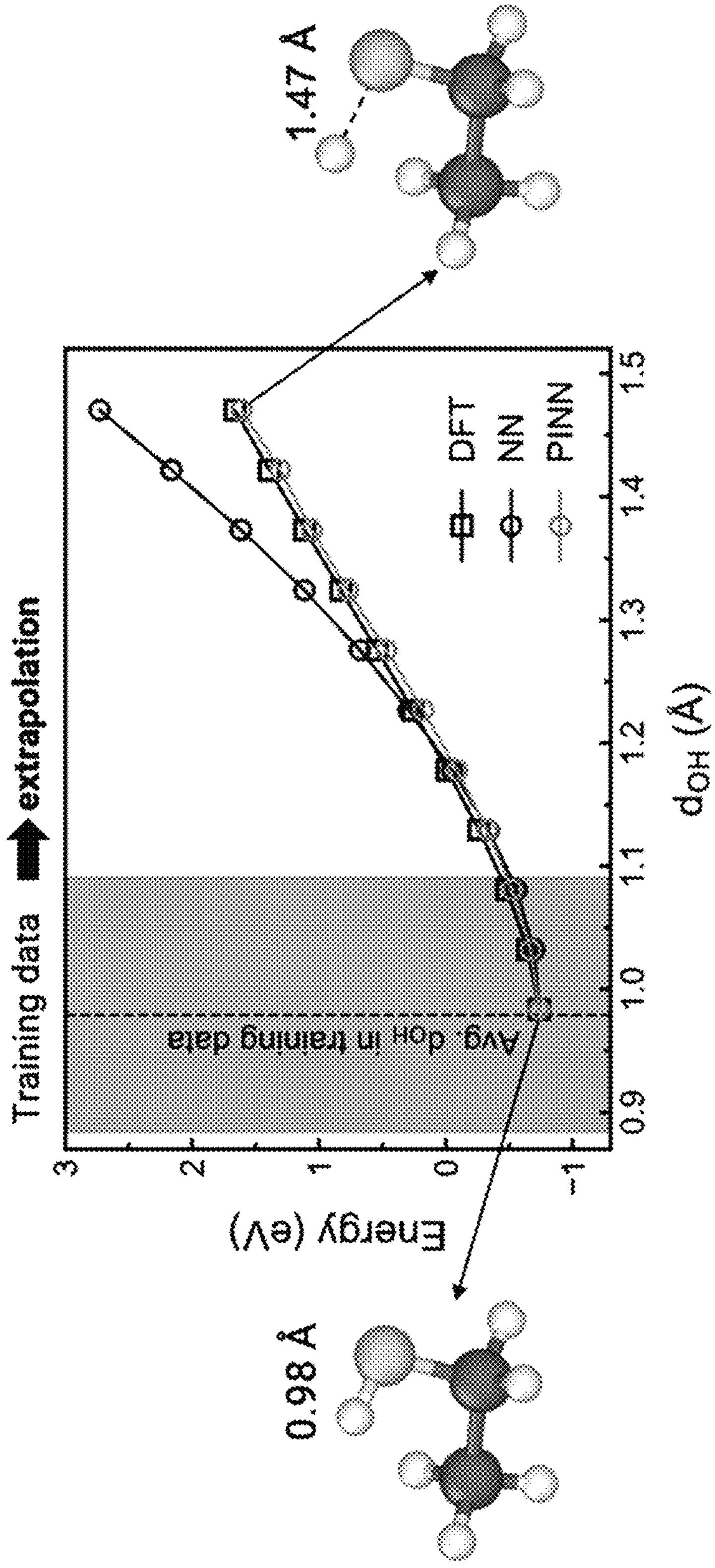
FIG. 11 is a graph showing the results of simulating the formation and destruction of chemical bonds by extrapolating the potential energy of malonaldehyde calculated using the physics-informed artificial neural network (PINN) model in Example 2.

FIG. 11 is a graphs showing the result of simulating formation and destruction of chemical bonds by extrapolating a potential energy of malonaldehyde, which is calculated by using the physics-informed artificial neural network (PINN) model.

In FIG. 11, DFT indicates a case of using the density functional theory (DFT), NN indicates a cate of using the conventional artificial neural network (NN) model, and PINN indicates a case of using the physics-informed artificial neural network (PINN) according to the preset aspect.

Referring to FIG. 11, when the physics-informed artificial neural network (PINN) model is used, even if directly unbonded structures are not included in learning data during the potential learning, tendency of structural energy changes may be effectively predicted. On the contrary, this may not be simulated by using the conventional artificial neural network (NN) model.

While this disclosure has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

We claim:

1. A method for predicting a potential energy of a multicomponent material, comprising:

encoding a structural information of a multicomponent material in which eigenvector values for each element are calculated using an atom-centered symmetry function (ACSF) of a structural information of atoms constituting the multicomponent material;

calculating a bond order potential (BOP) parameter for each element using the calculated eigenvector value as an input value and using a different artificial neural network model for each type of atom to construct a physics-informed artificial neural network (PINN) model;

calculating a bond order potential value for each element to construct a potential energy surface (PES); and performing structural optimization or physical property prediction of the multicomponent material using a potential energy surface; and synthesizing or purifying at least one of polymers, macromolecules, and compounds based on the structural optimization or physical property prediction, wherein each of the encoding, the calculating of the bond order potential parameter, the calculating of the bond order potential value, and the performing is performed by at least one of a central processing unit (CPU) and a graphics processing unit (GPU), for artificial neural network models different for each element, the artificial neural network parameter is optimized by applying backpropagation to a loss function represented by Equation 5, $$\text{Loss function } (L)\text{=error in potential energy value+ error in force value,} \quad \text{[Equation 5]}$$

in Equation 5, the error in potential energy value is a difference between the potential energy value calculated by the artificial neural network using a bond order potential model and a potential energy value of learning data, the error of the force value is a difference between a force value calculated by the artificial neural network using a bond order potential model and a force value of a learning data, the potential energy value of the bond order potential model is calculated using Equation 6, and the force value of the bond order potential model is calculated using Equation 7, $$E = \sum_{i}^{n} E_i \quad \text{[Equation 6]}$$

in Equation 6, E is a potential energy value for each atom, and is calculated by Equation 8, $$F = -\nabla_R E \quad \text{[Equation 7]}$$

in Equation 7, E is a total potential energy value of the multicomponent material, and $\nabla_R$ is a gradient of the potential energy E with respect to the position R of the atom, $$E_i = \frac{1}{2}\sum_{j\neq i}\left[e^{A_i-\alpha_i r_{ij}} - S_{ij} b_{ij} e^{B_i-\beta_i r_{ij}}\right] f_c(r_{ij}) + E_i^{(p)} \quad \text{[Equation 8]}$$

in Equation 8, $r_{ij}$ is a distance between atom i and atom j, $S_{ij}$ is calculated by Equation 9, $b_{ij}$ is calculated by Equation 11, $E_i^{(p)}$ is calculated by Equation 13, $f_c$ is a cut-off function and represented by Equation 3, and $A_i$, $\alpha_i$, $B_i$, and $\beta_i$ are one of the bond order potential parameters, $$S_{ij} = \prod_{k \neq i,j} S_{ijk} \quad \text{[Equation 9]}$$

in Equation 9, $S_{ijk}$ is calculated by Equation 10, $$S_{ijk} = 1 - f_c(r_{ik} + r_{jk} - r_{ij})e^{-\lambda_i^2(r_{ik}+r_{jk}-r_{ij})} \quad \text{[Equation 10]}$$

in Equation 10,
$f_c$ is a cut-off function and represented by Equation 3,
$r_{ij}$ is a distance between atom i and atom j,
$r_{ik}$ is a distance between atom i and atom k,
$r_{jk}$ is a distance between atom j and atom k, and
$\lambda_i$ is one of the bond order potential parameters, $$b_{ij}=(1+z_{ij})^{-1/2} \quad \text{[Equation 11]}$$

in Equation 11, $z_{ij}$ is calculated by Equation 12, $$z_{ij} = a_i^2 \sum_{k \neq i,j} S_{ik}(\cos\theta_{ijk} + h_i)^2 f_c(r_{ik}) \quad \text{[Equation 12]}$$

in Equation 12,
$a_i$ and $h_i$ are one of the bond order potential parameters,
$\theta_{ijk}$ is an angle between atom i, atom j, and atom k,
$f_c$ is a cut-off function and represented by Equation 3, and
$r_{ik}$ is a distance between atom i and atom k, $$E_i^{(p)} = -\sigma_i\left(\sum_{j \neq i} S_{ij} b_{ij} f_c(r_{ij})\right)^{1/2} \quad \text{[Equation 13]}$$

in Equation 13,
$\sigma_i$ is one of the bond order potential parameters,
$f_c$ is a cut-off function and represented by Equation 3, and
$r_{ij}$ is a distance between atom i and atom j, $$\text{when } r \neq r_c,\quad f_c = 0.5\left(1 + \cos\left(\pi\frac{r}{r_c}\right)\right),\quad \text{when } r > r_c,\quad fc = 0, \quad \text{[Equation 3]}$$

in Equation 3, r is a radius of a neighbor atom from a center atom, and $r_c$ is a cut-off radius to limit an influence on a center atom.

2. The method of claim 1, wherein
the encoding of the structural information of the multicomponent material includes
searching for atoms within a distance $r_{cut}$ (about 5 Å or less) from each atom in a three-dimensional atomic structure of the multicomponent material,
calculating a distance and angle between the atoms, and
calculating eigenvector values for each atom using the distance and angle between atoms as input values and using an atom-centered symmetry function (ACSF).

3. The method of claim 1, wherein
the atom-centered symmetry function (ACSF) is represented by Equation 1 or Equation 2:

$$G_i^{II,Z} = \sum_{j \in N_i^Z} e^{-\eta(r_{ij}-r_s)^2/r_c^2} f_c(r_{ij}) \quad \text{[Equation 1]}$$

wherein, in Equation 1,
$r_{ij}$ is a distance between atom i and atom j,
$r_c$ is a cut-off radius ($r_{cut}$) to limit an influence on a center atom,
$\eta$ is a variable that controls a reformation of a graph,
$N_i^Z$ is a set of atoms with atomic number z among neighbor atoms of atom i, and
$f_c$ is a cut-off function and is represented by Equation 3, $$G_i^{IV,Z_1,Z_2} = 2^{1-\zeta} \sum_{k \in N_i^{Z_2}} \sum_{j \in N_i^{Z_1}} (1 + \lambda\cos\theta_{ijk})^{\zeta} \cdot e^{-\eta(r_{ij}^2+r_{ik}^2+r_{jk}^2)/r_c^2} f_c(r_{ij}) f_c(r_{ik}) f_c(r_{jk}) \quad \text{[Equation 2]}$$

wherein, in Equation 2,
$r_{ij}$ is a distance between atom i and atom j,
$r_{ik}$ is a distance between atom i and atom k,
$r_{jk}$ is a distance between atom j and atom k,
$\theta_{ijk}$ is an angle between atom i, atom j, and atom k,
$r_c$ is a cut-off radius ($r_{cut}$) to limit an influence on a center atom,
$\eta$, $\lambda$, and $\zeta$ are variables that control a reformation of a graph,
$N_i^{Z1}$ is a set of atoms with atomic number $z_1$ among neighbor atoms of atom i,
$N_i^{Z2}$ is a set of atoms with atomic number $z_2$ among neighbor atoms of atom i, and
$f_c$ is a cut-off function and is represented by Equation 3, $$\text{when } r \neq r_c,\ fc = 0.5\left(1 + \cos\left(\pi\frac{r}{rc}\right)\right) \quad \text{when } r > r_c,\ fc = 0 \quad \text{[Equation 3]}$$

wherein, in Equation 3,
r is a radius of the neighbor atom from a center atom, and
$r_c$ is a cut-off radius ($r_{cut}$) to limit an influence on a center atom.

4. The method of claim 1, wherein
the bond order potential value for each element is represented by Equation 4:

$$p_i = (A_i, \alpha_i, B_i, \beta_i, a_i, \sigma_i, h_i, \lambda_i) \quad \text{[Equation 4]}$$

wherein, in Equation 4,
$A_i$, $\alpha_i$, $B_i$, $\beta_i$, $a_i$, $\sigma_i$, $h_i$, and $\lambda_i$ are one of bond order potential parameters.

5. The method of claim 1, wherein
in Equation 5, a ratio of the error in the potential energy value and the error in the force value is about 1:10 to about 1:100.

6. The method of claim 1, wherein
before learning the artificial neural network, a single bond order potential global parameter ($p^{0,s}$) is optimized for the entire learning data, and the artificial neural network calculates the local perturbation ($\delta p_i$) for each element, the artificial neural network calculates the local perturbation ($\delta p_i$) for each element, and the bond order potential (BOP) parameter is calculated by Equation 14:

$$p_i^s = p^{0,s} + \delta p_i^s \quad \text{[Equation 14]}$$

wherein, in Equation 14, $p^{0,s}$ is a bond order potential global parameter for each atom(s), and $\delta p_i$ is a local perturbation, and is calculated by Equation 15, $$\delta p_i = \theta_0 MLP^s(G_i)\ (\theta_0 \in R^8) \quad \text{[Equation 15]}$$

wherein, in Equation 15, $MLP^s(G_i)$ is a Value calculated from an artificial neural network model for each element type (s) when the input value $G_i$ is input, and $\theta_0$ is a learning scaling factor.

7. The method of claim 6, wherein the global parameter ($p^{0,s}$) includes 8 real values and is initialized to a random value and then optimized using Adam or BFGS (Broyden-Fletcher-Goldfarb-Shanno).

8. The method of claim 6, wherein the learning scaling factor ($\theta_0$) includes 8 real values, initial values of all 8 are 1.0, and the learning scale factor ($\theta_0$) is also learned by inputting it as an input value to the artificial neural network model.

9. The method of claim 1, wherein the constructing of the potential energy surface is performed by, using the bond order potential (BOP) parameter for each element, calculating the potential energy value using Equation 6, and calculating the force value using Equation 7.

* * * * *